(12) United States Patent
Sasady et al.

(10) Patent No.: US 11,324,477 B2
(45) Date of Patent: May 10, 2022

(54) MULTI-PURPOSE INSTRUMENT GUIDE

(71) Applicant: B-K Medical Aps, Herlev (DK)

(72) Inventors: Niels-Christian Sasady, Frederiksberg (DK); Per Ehrenreich Nygaard, Soeborg (DK); John Antol, Nahant, MA (US)

(73) Assignee: BK Medical APS, Herlev (DK)

( * ) Notice: Subject to any disclaimer, the term of this patent is extended or adjusted under 35 U.S.C. 154(b) by 657 days.

(21) Appl. No.: 15/303,654

(22) PCT Filed: Apr. 16, 2014

(86) PCT No.: PCT/IB2014/060781
§ 371 (c)(1),
(2) Date: Oct. 12, 2016

(87) PCT Pub. No.: WO2015/159129
PCT Pub. Date: Oct. 22, 2015

(65) Prior Publication Data
US 2017/0035385 A1 Feb. 9, 2017

(51) Int. Cl.
*A61B 8/00* (2006.01)
*A61B 8/08* (2006.01)
(Continued)

(52) U.S. Cl.
CPC .......... *A61B 8/0841* (2013.01); *A61B 8/4209* (2013.01); *A61B 17/3403* (2013.01);
(Continued)

(58) Field of Classification Search
CPC ................ A61B 8/0841; A61B 8/4209; A61B 2017/3403; A61B 2017/3405;
(Continued)

(56) References Cited

U.S. PATENT DOCUMENTS 4,475,553 A * 10/1984 Yamaguchi .......... A61B 8/0833
600/461
6,203,499 B1 * 3/2001 Imling ................. A61B 8/0833
600/461
(Continued)

FOREIGN PATENT DOCUMENTS

WO 2007110076 A1 10/2007
WO 2012088458 A1 6/2012

OTHER PUBLICATIONS

International Search Report for PCT/IB2014/060781 published as WO2015/159129A1 dated Oct. 22, 2015.

*Primary Examiner* — Rajeev P Siripurapu
(74) *Attorney, Agent, or Firm* — Daugherty & Del Zoppo Co., LPA

(57) ABSTRACT

An instrument guide (104) for a probe head (702) of an ultrasound imaging probe (106) that includes a transducer array (114) with a plurality of transducer elements (116) and an image plane. The instrument guide includes a probe support region (122) having a long axis (202) and configured to receive the probe head. The instrument guide further includes a first guide bracket (212) extending from a first side of the support region in a direction of the long axis. The instrument guide further includes a second guide bracket (230) extending from a second side of the support region in a direction transverse to the long axis. The instrument guide further includes a first guide (128) disposed in the first guide bracket. The instrument guide further includes a second guide (126) disposed in the second guide bracket.

23 Claims, 6 Drawing Sheets

(51) Int. Cl.
  *A61B 17/34* (2006.01)
  *A61B 34/20* (2016.01)
(52) U.S. Cl.
  CPC ...... *A61B 34/20* (2016.02); *A61B 2017/3405* (2013.01); *A61B 2017/3411* (2013.01); *A61B 2017/3413* (2013.01)
(58) Field of Classification Search
  CPC .... A61B 2017/3407; A61B 2017/3409; A61B 2017/3411; A61B 2017/3413; A61B 34/20; A61B 17/3403
  See application file for complete search history.

(56) References Cited

U.S. PATENT DOCUMENTS

| | | | |
|---|---|---|---|
| 7,691,066 B2 * | 4/2010 | Kosaku | A61B 8/0833 600/459 |
| 2007/0049822 A1 | 3/2007 | Bunce et al. | |
| 2009/0143684 A1 | 6/2009 | Cermak et al. | |
| 2011/0028847 A1 * | 2/2011 | Whitmore, III | A61B 17/3403 600/461 |
| 2012/0165679 A1 * | 6/2012 | Orome | A61B 8/4444 600/461 |
| 2014/0200445 A1 * | 7/2014 | Boezaart | A61M 5/158 600/424 |

\* cited by examiner

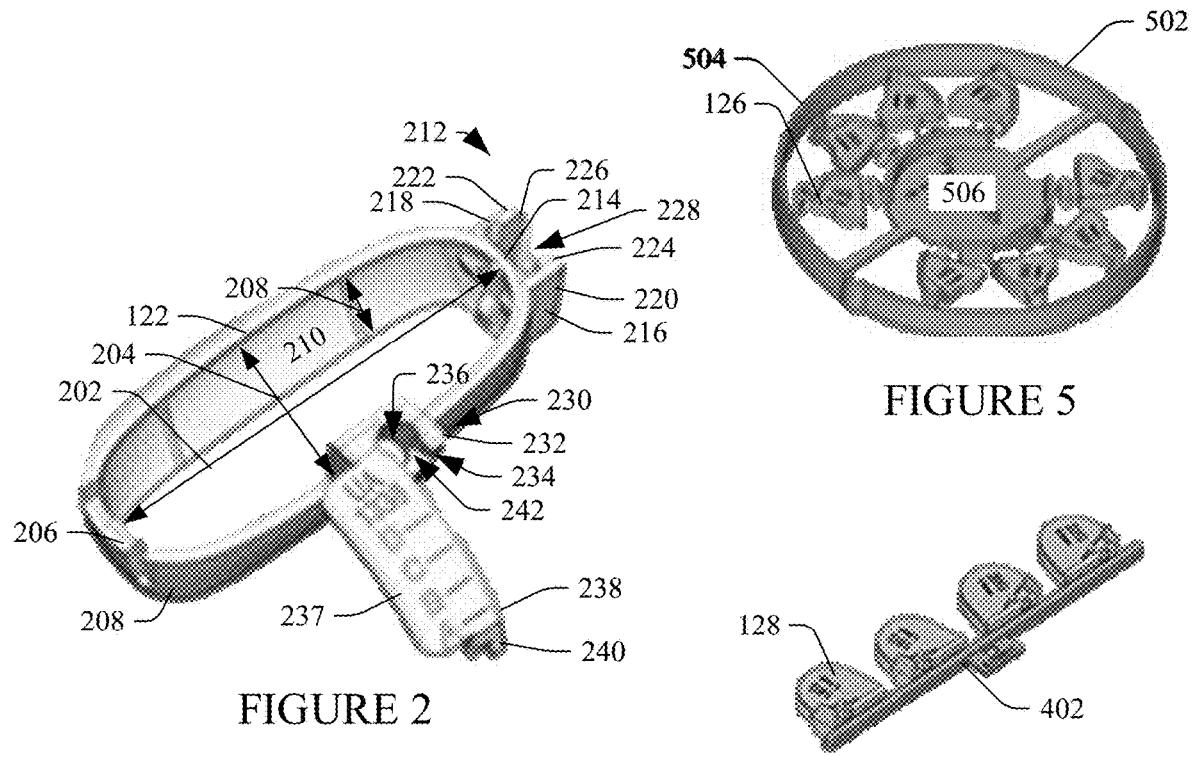
FIGURE 5
FIGURE 4
FIGURE 2
FIGURE 3
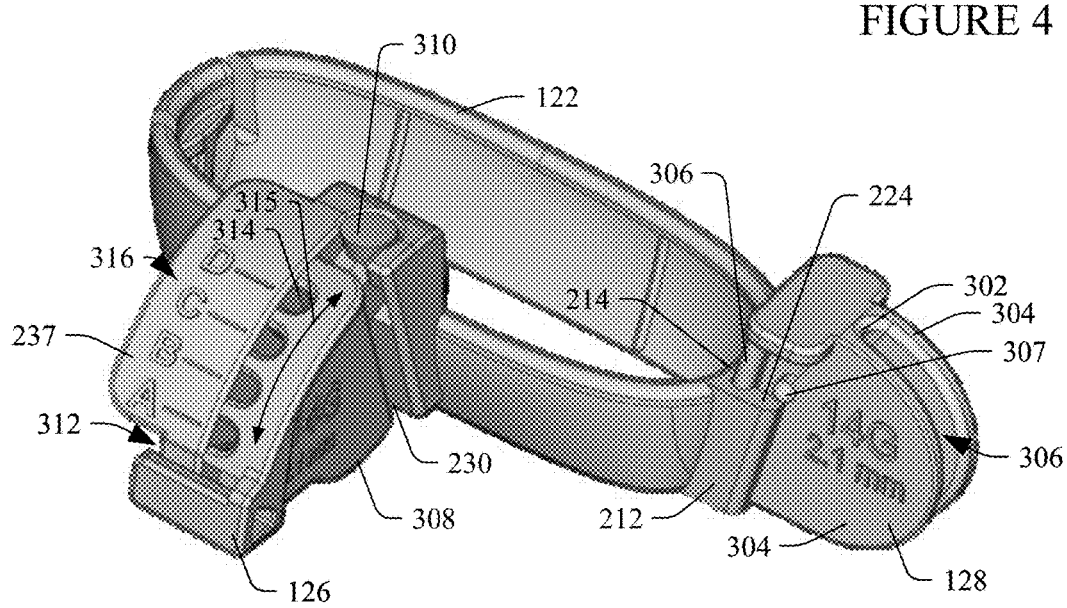

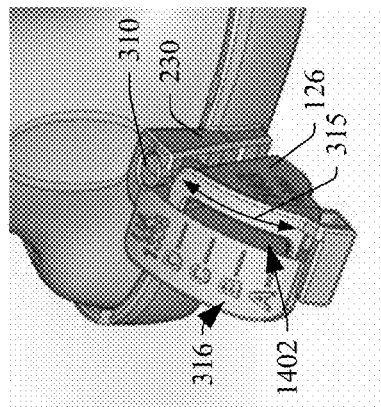
FIGURE 14
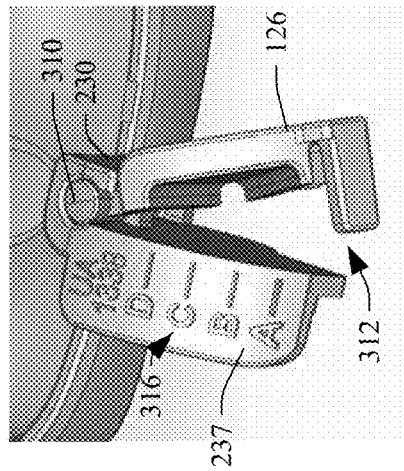
FIGURE 13
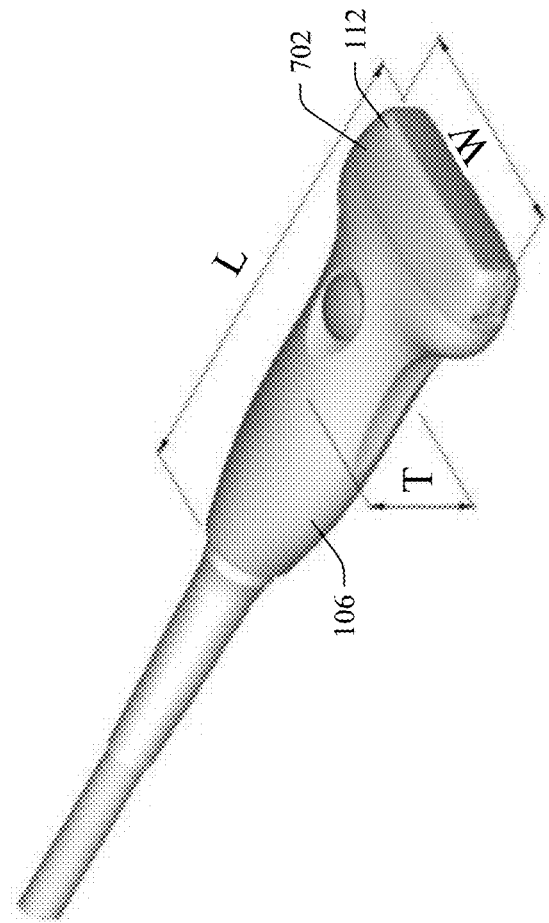
FIGURE 7
FIGURE 6

MULTI-PURPOSE INSTRUMENT GUIDE

RELATED APPLICATION

This application is a national filing of PCT application Serial No. PCT/IB2014/060781, filed Apr. 16, 2014, published as WO2015/159129 on Oct. 22, 2015. This application claims priority to PCT application Serial No. PCT/IB2014/060781, published as WO2015/159120 on Oct. 22, 2015.

TECHNICAL FIELD

The following generally relates to an instrument guide and more particular to a multi-purpose instrument guide that provides both in-plane and out-of-plane (transverse) guidance, and is described with particular application to ultra-sounds imaging. However, the following is also amenable to other imaging modalities.

BACKGROUND

An ultrasound imaging system has included an ultrasound probe and a console. The probe houses a transducer array, and the console includes a display monitor and a user interface. The transducer transmits an ultrasound signal into a field of view and receives echoes produced in response to the signal interacting with structure therein. The echoes are conveyed to the console and are processed, producing images of the scanned structure, which may be visually presented through the display monitor.

Ultrasound imaging has been used to assist in the proper placement of a catheter, a needle (e.g., an intravenous (I.V.) line), and/or other device. For example, an ultrasound image of a vessel and instrument can be used for in-plane (i.e., in the image plane of the transducer) or out-of-plane (i.e., transverse to the image plane of the transducer) visual guidance. However, it can be difficult to place the device using visual guidance alone. In such instance, a physical instrument guide can be used.

An example of an in-plane physical needle guide is the puncture guide attachment UA1234, which is a product of Analogic Corporation, Peabody, Mass., USA. Generally, the attachment UA1234 is a plastic guide with a needle channel and a slot to accommodate different sized needles and insertions at different angles. The puncture guide attachment UA1234 has been used with linear array transducer types 8559-S and 8659, both products of Analogic Corporation, Peabody, Mass., USA.

A user may want to initiate a procedure with an out-of-plane guide and then switch to an in-plane guide in order to see the long axis of the instrument. However, it may not be possible to know ahead of time which guide will be used for the procedure. Unfortunately, a user will have to select an initial guide up front, and if they choose to switch the guide, then the guide will need to be replaced during the procedure.

SUMMARY

Aspects of the application address the above matters, and others.

In one aspect, an instrument guide is for a probe head of an ultrasound imaging probe that includes a transducer array with a plurality of transducer elements and an image plane. The instrument guide includes a probe support region having a long axis and configured to receive the probe head. The instrument guide further includes a first guide bracket extending from a first side of the support region in a direction of the long axis. The instrument guide further includes a second guide bracket extending from a second side of the support region in a direction transverse to the long axis. The instrument guide further includes a first guide disposed in the first guide bracket. The instrument guide further includes a second guide disposed in the second guide bracket.

In another aspect, a method includes receiving, with a first guide of at least two guides of an instrument guide, a first instrument and guiding the first instrument with the first guide in an image plane of a transducer array. The method further includes receiving, with a second guide of the at least two guides of the instrument guide, a second instrument and guiding the second instrument with the second guide in a direction transverse to the image plane.

In another aspect, a system includes an ultrasound imaging system with at least an ultrasound probe that houses a transducer array. The system further includes an instrument guide that is configured to receive a sub-portion of ultrasound probe housing the transducer array. The instrument guide includes at least two guide brackets, one extending in an image plane of the ultrasound probe and the other extending in a direction transverse to the image plane. The instrument guide further includes a least two guides, one removably disposed in a first of the at least two guide bracket and another removably disposed in another of the at least two guide bracket.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIG. 2 illustrates an example of the instrument guide without in-plane and out-of-plane guides;

FIG. 3 illustrates an example of the instrument guide with an in-plane guide and an out-of-plane guide with fixed angle slots;

FIG. 4 illustrates an example of a plurality of in-plane guides;

FIG. 5 illustrates an example of a plurality of out-of-plane guides;

FIG. 6 illustrates a perspective view of the instrument guide installed on an transducer probe;

FIG. 7 illustrates an example of the transducer probe;

FIG. 13 illustrates an example of the out-of-plane guide in an "open" position; and FIG. 14 illustrates an example of the out-of-plane guide with a free angle slot.

DETAILED DESCRIPTION

Figure 1:
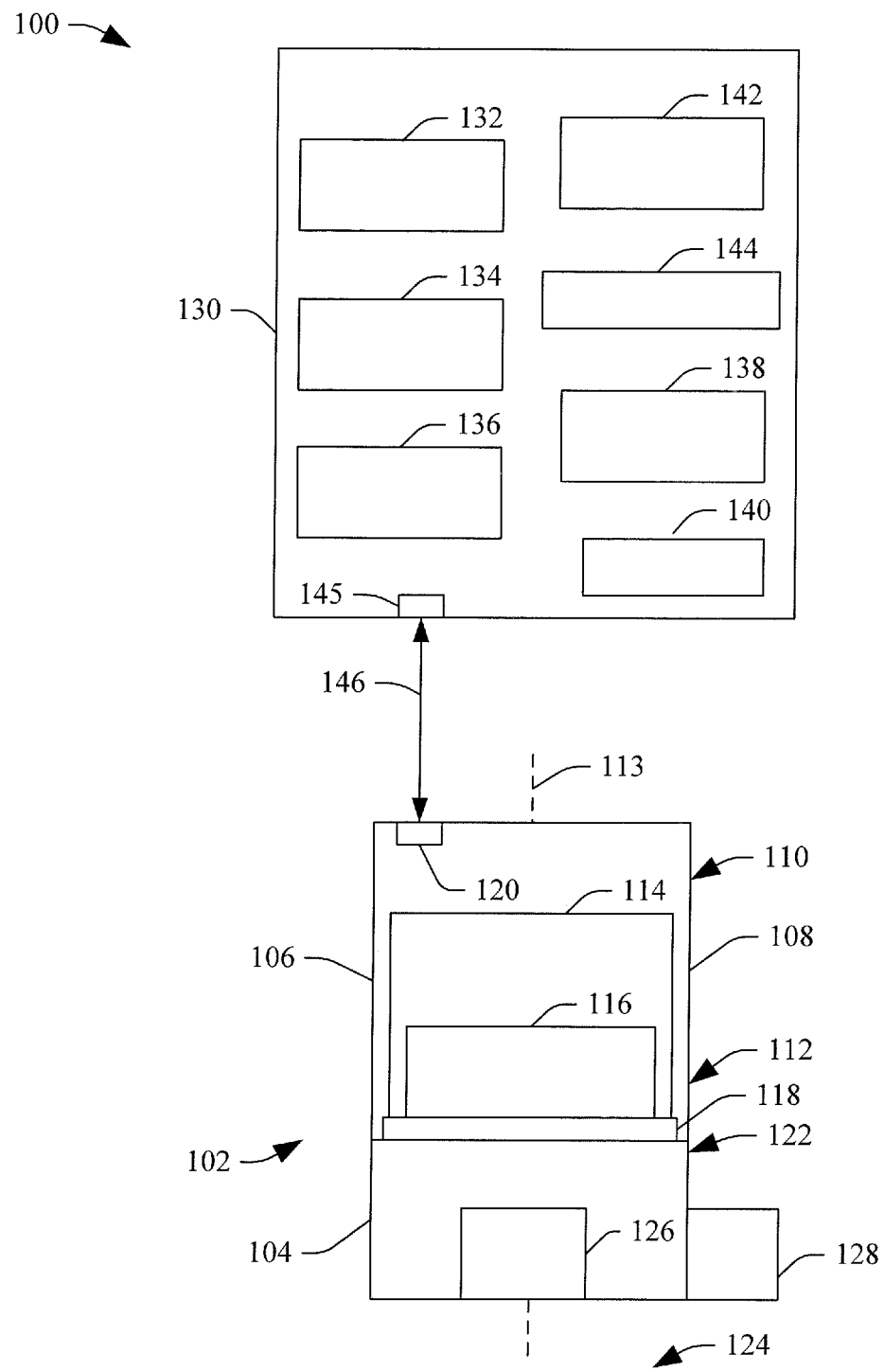
FIG. 1 schematically illustrates a system including an example instrument guide in connection with an ultrasound imaging system.

FIG. 1 schematically illustrates a system 100, which includes an example imaging system 102 in connection with an instrument guide 104. The illustrated imaging system 102 includes an ultrasound imaging system, which includes, in this example, a probe 106 and a console 130, which are in electrical communication with each other. Examples of suitable instrument guides 104 include instrument guides for catheters, needles, and/or other instruments.

The probe 106 has a structural housing 108 that includes a first end region 110 and a second end region 112, and a long axis 113. The housing 108 houses and physically supports a transducer array 114. The illustrated transducer array 114 includes a linear array with a plurality of transducer elements 116 (e.g., 64, 128, 192, etc.). However, other arrays, like convex linear, sector, etc. arrays are also contemplated herein. The transducer array 114 can be fully populated and/or sparse. The transducer elements 116 transmit ultrasound signals and receive echo signals.

The probe 106 further includes an ultrasonic window 118, which is located at the second end region 112. The ultrasonic window 118 can be part of and/or integrated with the housing 108. Ultrasound signals and receive echo signals traverse through the ultrasonic window 118. The probe 106 further includes a console interface 120 such as an electromechanical connector and/or a wireless transceiver. The electro-mechanical connector can be mounted to or removably connectable to a cable or the like.

The instrument guide 104 includes a probe support region 122 that removably affixes to the second end region 112 of the probe 106 and allows ultrasound and echo signals to traverse between the ultrasonic window 118 and an examination region 124, unimpeded. The instrument guide 104 further includes an out-of-plane guide 126 and an in-plane guide 128. Herein, out-of-plane refers to a direction transverse to an image plane of the transducer array 114, and in-plane refers to a direction in this image plane.

As described in greater detail below, the out-of-plane guide 126 and the in-plane guide 128 provide a dual purpose instrument guide 104. The out-of-plane guide 126 and/or the in-plane guide 128 removably affix to the instrument guide 104, and can be interchanged with another out-of-plane guide 126 and/or in-plane guide 128. This allows for selecting a guide based on instrument gauge size, instrument insertion angle (e.g., free or fixed), etc. Furthermore, the instrument guide 104 is sterile and disposable.

The imaging system 102 further includes a console 130. The console 130 includes transmit circuitry 132 that selectively actuates or excites one or more of the transducer elements 116. More particularly, the transmit circuitry 132 generates a set of pulses (or a pulsed signal) that are conveyed to the transducer elements 116. The set of pulses actuates a set of the transducer elements 116, causing the transducer elements 116 to transmit ultrasound signals into an examination or scan field of view.

The console 130 further includes receive circuitry 134 that receives a set of echoes (or echo signals) generated in response to the transmitted ultrasound signals. The echoes, generally, are a result of the interaction between the emitted ultrasound signals and the object (e.g., flowing blood cells, organ cells, etc.) in the scan field of view. The receive circuitry 134 may be configured for spatial compounding, filtering (e.g., FIR and/or IIR), and/or other echo processing.

An echo processor 136 processes the received echoes. In B-mode, this includes applying time delays and weights to the echoes and summing the delayed and weighted echoes. A scan converter 138 scan converts the data for display, e.g., by converting the beamformed data to the coordinate system of a display or display region used to visually present the resulting data. A display 140 visually displays the ultrasound image. The ultrasound image can be used to guide an instrument with respect to a subject or object.

A user interface (UI) 142 include one or more input devices (e.g., a button, a knob, a touchscreen, etc.) and/or one or more output devices (e.g., a display monitor, an audio presenter, etc.), which allows for interaction with the system 102. A controller 144 controls the various components of the system 102. A probe interface 145 includes an electromechanical connector and/or wireless transceiver. The console and probe interfaces 120 and 145 are connected via a communications path 146.

At least one of the components of the console 130 can be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

FIGS. 2 and 3 show an example of the instrument guide 104 respectively without and with the out-of-plane guide 126 and the in-plane guide 128. FIGS. 4 and 5 respectively show a plurality of out-of-plane guides 126 and a plurality of in-plane guides 128.

Initially referring to FIG. 2, the probe support region 122 has a geometry that is complementary to a geometry of the second end region 112 of the probe 106. In the illustrated embodiment, this geometry is elliptical with a long axis 202 and a short axis 204. In a variation, the geometry is rectangular, square, etc. The region 122 also includes a wall 206 that tapers along a depth 208. The wall 206 includes an outer wall 209 and an inner wall 210, which, when the instrument guide 104 is installed on the probe 106, physically contacts the second end region 112.

The instrument guide 104 further includes an in-plane guide support bracket 212. The bracket 212 includes a sub-portion 214 of the outer wall 208 and first and second protrusions 216 and 218 that protrude therefrom. The first and second protrusions 216 and 218 are spaced apart from each other by a non-zero distance and extend out of the support region 122 along the long axis 206. Free ends 220 and 222 of the protrusions have inward facing protruding members 224 and 226, which extend towards each other along a direction of the short axis 204.

A combination of the sub-portion 214, the first and second protrusions 216 and 218, and the inward facing protruding members 224 and 226 form an opening 228 configured to alternatively receive and engage one or a plurality of different in-plane guides 128, each structurally similar, but configured for a different gauge size instrument. The opening 228 receives an in-plane guide 128 in a direction along the depth 208 of the support region 122. The inward facing protruding members 224 and 226 inhibit movement of the in-plane guide 128 along a direction of the long axis 210. The sub-portion 214 also includes a feature (e.g., a hole), which together with a tap on the in-plane guide 128 locks this in position when correctly mounted. In FIG. 2, the feature and the tap are not visible.

The instrument guide 104 further includes an out-plane guide support bracket 230. The illustrated out-plane guide support bracket 230 includes a protrusion 232 that protrudes out of a first end of the support region 122 in a direction along the depth 208 and away from the probe support region 122. The protrusion 232 includes a cut out 234 and a material free region or recess 236. The out-plane guide support bracket 230 also includes a tab 237 that extends from the protrusion 232 away from the support region 122 along the short axis 204. A free end 238 of the tab 237 includes a securing mechanism 240.

A combination of the protrusion 232, the cut out 234 and the recess 236 form a slot 242 configured to alternatively receive and engage one or a plurality of different out-of-plane guides 126, each structurally similar, but configured for a different gauge size instrument. The slot 242 receives an out-of-plane guide 126 in a direction along the short axis 204 of the support region 122. The recess 236 and the securing mechanism 240 secure an installed out-of-plane guide 126 to the instrument guide 104.

Turning now to FIG. 3, the instrument guide 104 of FIG. 2 is shown with the out-of-plane guide 126 and the in-plane guide 128 installed in the brackets 230 and 212.

The in-plane guide 128 includes a back wall 302 and two side walls 304 that protrude therefrom and are spaced apart from each other by a non-zero distance. The back wall 302 includes protrusions 306 (only one visible), which slide between the sub-portion 214 and the members 224 and 226 (not visible), and one or more stoppers 308, which prevent the back wall 302 from sliding completely through the bracket 212.

The three walls 302 and 304 form an elongate curved (e.g., nearly semi-circular) free angle slot 306. The spacing between the walls 304 corresponds to a gauge size of an instrument plus a margin. For example, the walls 304 of an in-plane guide for a 14 gauge (G) needle (as shown in FIG. 3) will have a spacing on the order of 2.1 millimeter (mm), which will allow a 14 gauge needle to traverse the free angle slot 306 from any angle along the curvature of the free angle slot 306, while prohibiting out of the image plane movement of the instrument. As such, the in-plane guide 128 keeps the instrument in the image plane.

Briefly turning to FIG. 4, a plurality of in-plane guides 128 are removably attached to a carrier 402. The plurality of in-plane guides 128 may include same gauge or at least two different gauge guides. In this example, an in-plane guide 128 is attached to a linear strip of the carrier 402. An in-plane guide 128 can be removed by twisting the in-plane guide 128 until the in-plane guide 128 becomes unfastened from the carrier 402 and/or otherwise.

Returning to FIG. 3, the out-of-plane guide 126 includes a body 308, a member 310, which protrudes out of a back of the body 310, and a tap 312. When the out-of-plane guide 126 is installed in the bracket 230, the first member 310 of the guide 126, is in the recess 236 (FIG. 2), and the securing mechanism 240 (FIG. 2) is in the tap 312. The combination thereof secures the guide 126 in place.

To install the guide 126, the out-of-plane guide 126 is aligned with the recess 236 and pushed downwards in the direction of the centerline of the member 310 until the tap 312 mates with the securing mechanism 240 with an audible "click". The guide 126 can be "open" for release of the needle by activating the tap 312 and turn the guide 126 around the body 310 by an angle until it stops against the wall in the recess 234. When "opened", the guide 126 is locked by a recess which is in the slot 234. This may prevent the guide 126 from falling out of the guide 104. FIG. 13 shows an example with the out-of-plane guide 126 (of FIG. 14, which is described below) in the "open" position.

The illustrated out-of-plane guide 126 includes a plurality of fixed angle slots 314, each at a different fixed angle with respect to the image plane. The illustrated out-of-plane guides 126 include four (4) fixed angle slots 314 that cover an arc 315. The tap 237 includes indicia 316, which identifies an angle of each of the slots 314. In a variation, the out-of-plane guide 126 includes a free angle slot 1402 that spans the same arc 315, as shown in FIG. 14, or a different arc. In a variation, the out-of-plane guide 126 instead includes a free angle slot, like the in-plane guides 128, but in the transverse direction. In another variation, the out-of-plane guide 126 can include at least one fixed angle and a free angle slot.

Briefly turning to FIG. 5, a plurality of out-of-plane guides 126 are removably attached to a carrier 502. The plurality of out-of-plane guides 126 may include same gauge or at least two different gauge guides. In this example, each of the out-of-plane guides 126 is attached to an inner ring 506 of the carrier 502. An outer ring 504 protects the guides 126, for example, from unexpected removal. An out-of-plane guide 126 can be removed by twisting the out-of-plane guide 126 until the out-of-plane guide 126 becomes unfastened from the carrier 502 and/or otherwise.

Turning to FIG. 6, the instrument guide 104 is shown installed with the ultrasound probe 106. As shown, the second end region 112 (FIG. 1) of the ultrasound probe 106, when the instrument guide 104 is installed on the probe 106, sits in probe support region 122 (FIGS. 1, 2 and 3) of the instrument guide 104.

FIG. 7 shows an example of a suitable probe 106. The example probe 106 is the 14L3, product data type 9051, a product of Analogic Corporation, Peabody, Mass., USA. This probe has a length "L" of 9.5 centimeters (cm) and a thickness "T" of 2.5 cm. A probe head 702, which houses and physically supports the transducer array 114, has a width "W" of 5.2 cm, with a contact surface of 4.5 cm. The probe head 702 includes the second end region 112, which is received in the probe support region 122.

Figure 8:
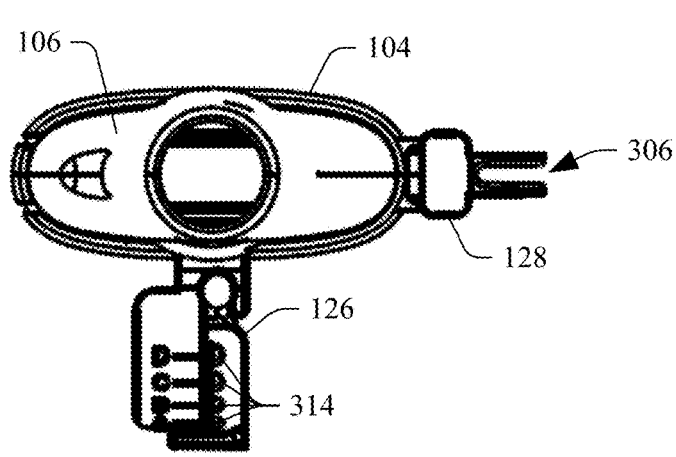
FIG. 8 schematically illustrates a top down view of the instrument guide installed on the transducer probe.
Figure 9:
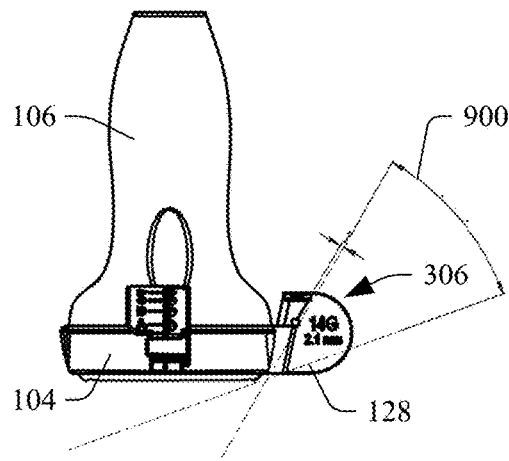
FIG. 9 schematically illustrates a front view of the instrument guide installed on the transducer probe.
Figure 10:
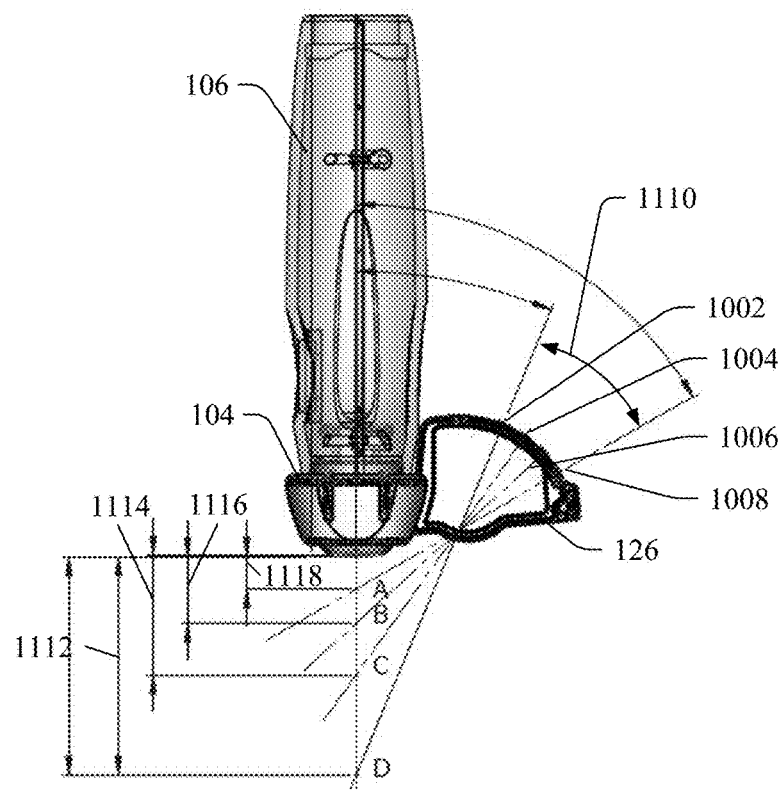
FIG. 10 schematically illustrates a side view of the instrument guide installed on the transducer probe.

FIGS. 8, 9 and 10 respectively a top down view, a front view, and a side view of the probe 106 and the instrument guide 104. These views show the out-of-plane guide 126 and the in-plane guide 128. FIG. 8 shows the free angle open slot 306 in the in-plane guide 128 and the fixed slots 314 in the out-of-plane guide 126.

FIG. 9 shows an example in which the free angle open slot 306 provides a free angle range 900 with respect to the image plane of the transducer array 114. In one instance, the free angle range 900 can be from 30 to 50 degrees, such as 38 degrees, 40 degrees, etc. In other embodiments, the free angle range may be larger or smaller.

FIG. 10 shows an example in which the fixed slots 314 provide a fixed set of angles 1002, 1004, 1006, and 1008 over a range 1110 with respect to the image plane of the transducer array 114. In one instance, the angle range 1110 can be 30 to 50 degrees, such as 35 degrees, 37.5 degrees, etc. In other embodiments, the free angle range may be larger or smaller.

In FIG. 10, the fixed angles 314 cross the plane of the beam at fixed depths 1112, 1114, 1116 and 118. Examples of suitable depths include, but are not limited to 5.7 mm, 11.7 mm, 21.1 mm, and 38.4 mm, and/or other depths. The same indicia from the tap 237 in FIG. 3 is shown with a corresponding fixed depth 1112, 1114, 1116 or 1118 in FIG. 10.

Figure 11:
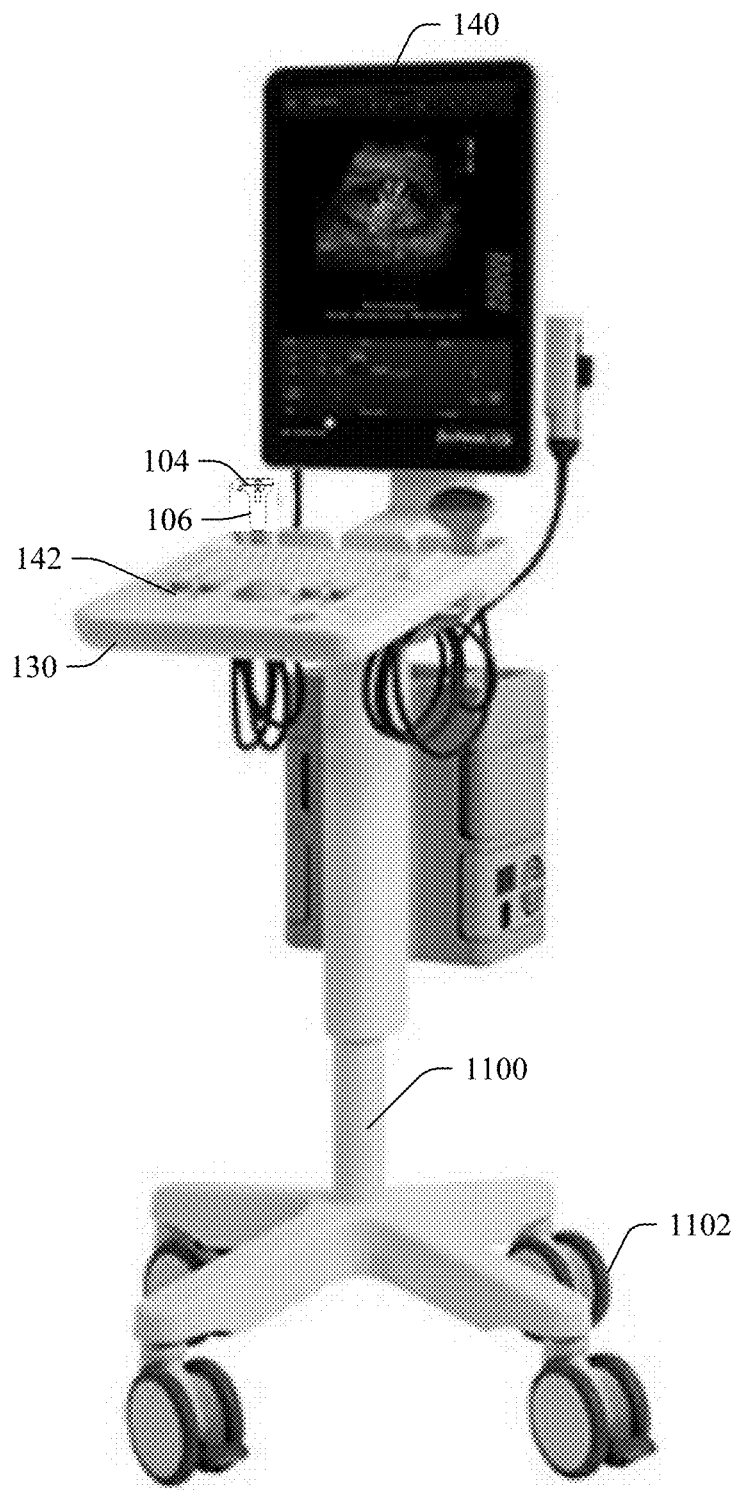
FIG. 11 illustrates an example of the ultrasound imaging system.

FIG. 11 illustrates a non-limiting example of the ultrasound imaging system 102, including the probe 106 with the instrument guide 104 installed thereon. In the non-limiting examples, the display monitor 140 and the ultrasound scanner console 130 are integrated with and part of a mobile cart 1100, which include movers 1102 such as wheels, casters, etc. In another configuration, the ultrasound imaging system 102 rests on a table, desk, etc., and does not include movers and is not integrated into a cart.

Figure 12:
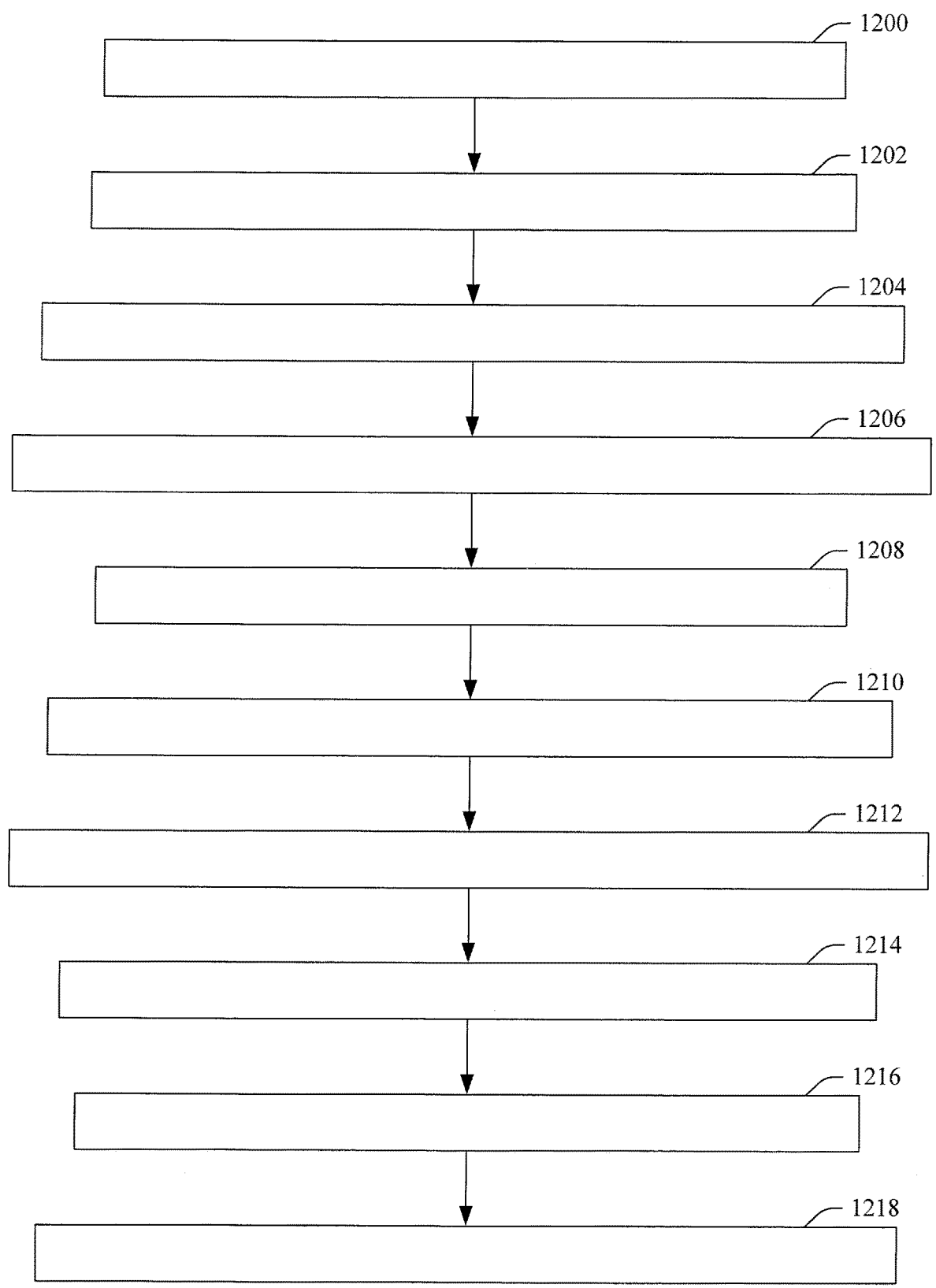
FIG. 12 illustrates example method.

FIG. 12 illustrates an example method.

It is to be appreciated that the ordering of the below acts is for explanatory purposes and not limiting. As such, other orderings are also contemplated herein. In addition, one or more of the acts may be omitted and/or one or more other acts may be included.

At 1200, an instrument guide for an ultrasound probe is obtained.

At 1202, the ultrasound probe, optionally, is covered with a protective sheet

At 1204, an in-plane guide of interest is removably affixed to the instrument guide.

At 1206, an out-of-plane guide of interest is removably affixed to the instrument guide, in a direction transverse to the in-plane guide.

At 1208, the instrument guide is installed on an ultrasound probe.

At 1210, an ultrasound image generated from data acquired by the ultrasound probe is used to locate structure in a subject or object.

At 1212, an instrument is installed in one of the instrument guides.

At 1214, the ultrasound image is used to align the instrument with the structure.

At 1216, the guide (and/or the image) is used to guide the instrument to the structure.

At 1218, the instrument guide is discarded when the procedure is complete.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An instrument guide for a probe head of an ultrasound imaging probe that includes a transducer array with a plurality of transducer elements that produces an image plane, the instrument guide, comprising:
   a probe support region having a long axis, a short axis, a depth, a first side at one end of the long axis, and a second side at one end of the short axis, wherein the short axis is transverse to the long axis and the depth, and configured to receive the probe head;
   a first guide bracket extending from the first side of the probe support region in a direction of the long axis;
   a first guide disposed in the first guide bracket;
   a second guide bracket on the second side of the probe support region and protruding out of and up from the second side in a direction of the short axis and the depth, wherein the second guide bracket includes:
      a slot, including:
         a protrusion protruding up from a top of the second side in a direction of the depth;
         a cut out of the protrusion; and
         a recess of the protrusion; and
      an arc shaped tab that extends from a top of the protrusion away from the probe support region along the short axis and including a free end with a portion extending from the arc shaped tab along the depth; and
   a second guide disposed in the second guide bracket, wherein the second guide includes:
      a body with a first end and a second end, which opposes the first end, along the short axis,
      a member protruding out of the body at the first end along the depth,
      a tap at the second end;
      an arc shaped surface extending between the first end and the second end along the short axis and the depth and disposed partially under the arc shaped tab; and
      a plurality of fixed slots in the surface arranged along the arc shaped surface and in the direction of the short axis, wherein each of the plurality of slots corresponds to a different fixed insertion angle with respect to the image plane,
   wherein the member of the second guide is disposed in the slot of the second guide bracket and the portion of the free end of the second guide bracket is disposed in the tap of the second guide.

2. The instrument guide of claim 1, wherein the first guide is an in-plane instrument guide.

3. The instrument guide of claim 2, the in-plane instrument guide, comprising:
   side walls extending from side of the probe support region in the direction of the long axis.

4. The instrument guide of claim 3, wherein the side walls are separated from each other by a distance that corresponds to an instrument gauge size.

5. The instrument guide of claim 4, wherein the separation forms a free angle slot.

6. The instrument guide of claim 4, wherein the first guide bracket includes an opening and the first guide is removably disposed in the opening.

7. The instrument guide of claim 1, wherein the second guide is an out-of-plane instrument guide.

8. The instrument guide of claim 1, wherein the member of the second guide is disposed in the slot of the second guide bracket along the depth of the slot of the probe support region.

9. The instrument guide of claim 1, wherein each of the plurality of fixed slots has a geometry that corresponds to a different gauge size of an instrument being guided by the second guide.

10. The instrument guide of claim 7, the out-of-plane instrument guide, further comprising:
    a free angle slot that extends in the direction of the short axis.

11. The instrument guide of claim 10, wherein the free angle slot has a geometry that corresponds to a gauge size of an instrument being guided by the second guide.

12. The instrument guide of claim 8, wherein the portion of the free end mates with the tap, which secures the second end of the second guide to the second guide bracket.

13. The instrument guide of claim 1, wherein the member of the second guide is rotatably coupled in the slot of the second guide bracket and configured to pivot between at least a first position in which the tap engages the portion of the free end and a second position in which the tap is disengaged from the portion of the free end.

14. The instrument guide of claim 13, wherein the second guide is locked by the recess of the slot when the portion of the free end is disengaged from the tap.

15. The instrument guide of claim 1, wherein the probe support region is elliptical shaped.

16. The instrument guide of claim 1, wherein the probe support region includes a wall that tapers along the depth.

17. The instrument guide of claim 16, wherein the wall includes an outer wall and an inner wall, and the first guide bracket includes a first sub-portion of the outer wall.

18. The instrument guide of claim 1, wherein the slot is configured to alternatively receive and engage one of a plurality of different out-of-plane guides, each configured for a different gauge size instrument.

19. The instrument guide of claim 1, wherein the tap includes indicia that identifies an angle of each of the plurality of fixed slots.

20. The instrument guide of claim 5, wherein the free angle slot is configured to provide a free angle range from 30 to 50 degrees.

21. The instrument guide of claim 1, wherein the fixed angle slots includes angles in a range from 30 to 50 degrees.

22. An instrument guide for a probe head of an ultrasound imaging probe that includes a transducer array with a plurality of transducer elements that produces an image plane, the instrument guide, comprising:
   a probe support region having a long axis, a short axis, a depth, a first side at one end of the long axis, and a second side at one end of the short axis, wherein the short axis is transverse to the long axis and the depth, and configured to receive the probe head;
   a first guide bracket extending from the first side of the probe support region in a direction of the long axis;
   a first guide disposed in the first guide bracket;
   wherein the probe support region further includes a second protrusion protruding out of and from the second side, wherein the second protrusion is part of the probe support region and is a second guide bracket protruding out of and up from the second side in a direction of the short axis and the depth, wherein the second guide bracket includes:
      a slot, including:
         a protrusion protruding up from a top of the second side in a direction of the depth;
         a cut out of the protrusion; and
         a recess of the protrusion; and
      an arc shaped tab that extends from a top of the protrusion away from the probe support region along the short axis and including a free end with a portion extending from the arc shaped tab along the depth; and
   a second guide disposed in the second guide bracket, wherein the second guide includes:
   a body with a first end and a second end, which opposes the first end, along the short axis,
      a member protruding out of the body at the first end along the depth,
      a tap at the second end;
      an arc shaped surface extending between the first end and the second end along the short axis and the depth and disposed partially under the arc shaped tab; and
      a plurality of fixed slots in the surface arranged along the arc shaped surface and in the direction of the short axis, wherein each of the plurality of slots corresponds to a different fixed insertion angle with respect to the image plane,
wherein the member of the second guide is disposed in the slot of the second guide bracket and the portion of the free end of the second guide bracket is disposed in the tap of the second guide.

23. An instrument guide for a probe head of an ultrasound imaging probe that includes a transducer array with a plurality of transducer elements that produces an image plane, the instrument guide, comprising:
   a probe support region having a long axis, a short axis, a depth, a first side at one end of the long axis, and a second side at one end of the short axis, wherein the short axis is transverse to the long axis and the depth, and configured to receive the probe head;
   wherein the probe support region further includes a first protrusion protruding out of and from the first side, wherein the first protrusion is part of the probe support region and is a first guide bracket extending out of the first side of the probe support region in a direction of the long axis;
   a first guide disposed in the first guide bracket;
   wherein the probe support region further includes a second protrusion protruding out of and from the second side, wherein the second protrusion is part of the probe support region and is a second guide bracket protruding out of and up from the second side in a direction of the short axis and the depth, wherein the second guide bracket includes:
      a slot, including:
         a protrusion protruding up from a top of the second side in a direction of the depth;
         a cut out of the protrusion; and
         a recess of the protrusion; and
      an arc shaped tab that extends from a top of the protrusion away from the probe support region along the short axis and including a free end with a portion extending from the arc shaped tab along the depth; and
   a second guide disposed in the second guide bracket, wherein the second guide includes:
   a body with a first end and a second end, which opposes the first end, along the short axis,
      a member protruding out of the body at the first end along the depth,
      a tap at the second end;
      an arc shaped surface extending between the first end and the second end along the short axis and the depth and disposed partially under the arc shaped tab; and
      a plurality of fixed slots in the surface arranged along the arc shaped surface and in the direction of the short axis, wherein each of the plurality of slots corresponds to a different fixed insertion angle with respect to the image plane,
wherein the member of the second guide is disposed in the slot of the second guide bracket and the portion of the free end of the second guide bracket is disposed in the tap of the second guide.

\* \* \* \* \*